United States Patent [19]

Williams

[11] Patent Number: 4,685,463

[45] Date of Patent: Aug. 11, 1987

[54] DEVICE FOR CONTINUOUS IN VIVO MEASUREMENT OF BLOOD GLUCOSE CONCENTRATIONS

[76] Inventor: R. Bruce Williams, One Stonehaven Dr., Signal Mountain, Tenn. 37377

[21] Appl. No.: 847,479

[22] Filed: Apr. 3, 1986

[51] Int. Cl.[4] ............................................. A61B 5/00
[52] U.S. Cl. ................................. 128/632; 128/736; 604/8; 604/50
[58] Field of Search ................... 128/632, 635, 736; 604/50, 66, 65, 67, 6–8, 264

[56] References Cited

U.S. PATENT DOCUMENTS

| | | | |
|---|---|---|---|
| 3,623,960 | 11/1971 | Williams | 128/635 X |
| 4,240,438 | 12/1980 | Updike et al. | 128/635 |
| 4,265,249 | 5/1981 | Schindler et al. | 128/635 |
| 4,340,615 | 7/1982 | Goodwin et al. | 128/635 X |
| 4,366,033 | 12/1982 | Richter | 204/1 T |
| 4,403,984 | 9/1983 | Ash et al. | 128/632 X |
| 4,431,004 | 2/1984 | Bessman | 128/635 |
| 4,436,094 | 1/1982 | Cerami | 128/635 |
| 4,440,175 | 4/1984 | Wilkins | 128/635 |
| 4,458,686 | 7/1984 | Clark, Jr. | 128/635 |
| 4,477,314 | 10/1984 | Richter | 204/1 T |
| 4,512,349 | 4/1985 | Hunt et al. | 128/635 X |

OTHER PUBLICATIONS

Article entitled "Use of an Enzyme Thermister in Continuous Measurements and Enzyme Reactor Control", by Bengt Danielsson, Bo Mattiasson, Roland Karlsson, and Fredrik Winqvist, Biochemistry 2, Chemical Center, University of Lund, Box 740, S–220 07 Lund 7, Sweden, published in the magazine Biotechnology and Bioengineering, vol. XXI, pp. 1749–1766, (1979)—Accepted for publication Nov. 27, 1978.

Primary Examiner—Kyle L. Howell
Assistant Examiner—Angela D. Sykes
Attorney, Agent, or Firm—Luedeka & Neely

[57] ABSTRACT

A device is disclosed for continuous in vivo measurement of blood glucose concentrations in arterial blood. A quantity of glucose oxidase enzyme is confined within at least one elongate double-lumened tube by means of a semi-permeable membrane tubule permeable to permit diffusion of glucose from blood passing through an inner lumen of the tube into an outer lumen in which the enzyme is confined. The enzyme catalyzes the oxidation of glucose to produce heat. The tube is insulated so that the heat produced by the glucose oxidation is transferred to the blood flowing through the inner lumen. Either micro-thermocouples or solid state temperature sensors are positioned to measure the increase in temperature of the blood to produce a signal that is a function of the glucose concentration in the blood.

12 Claims, 6 Drawing Figures

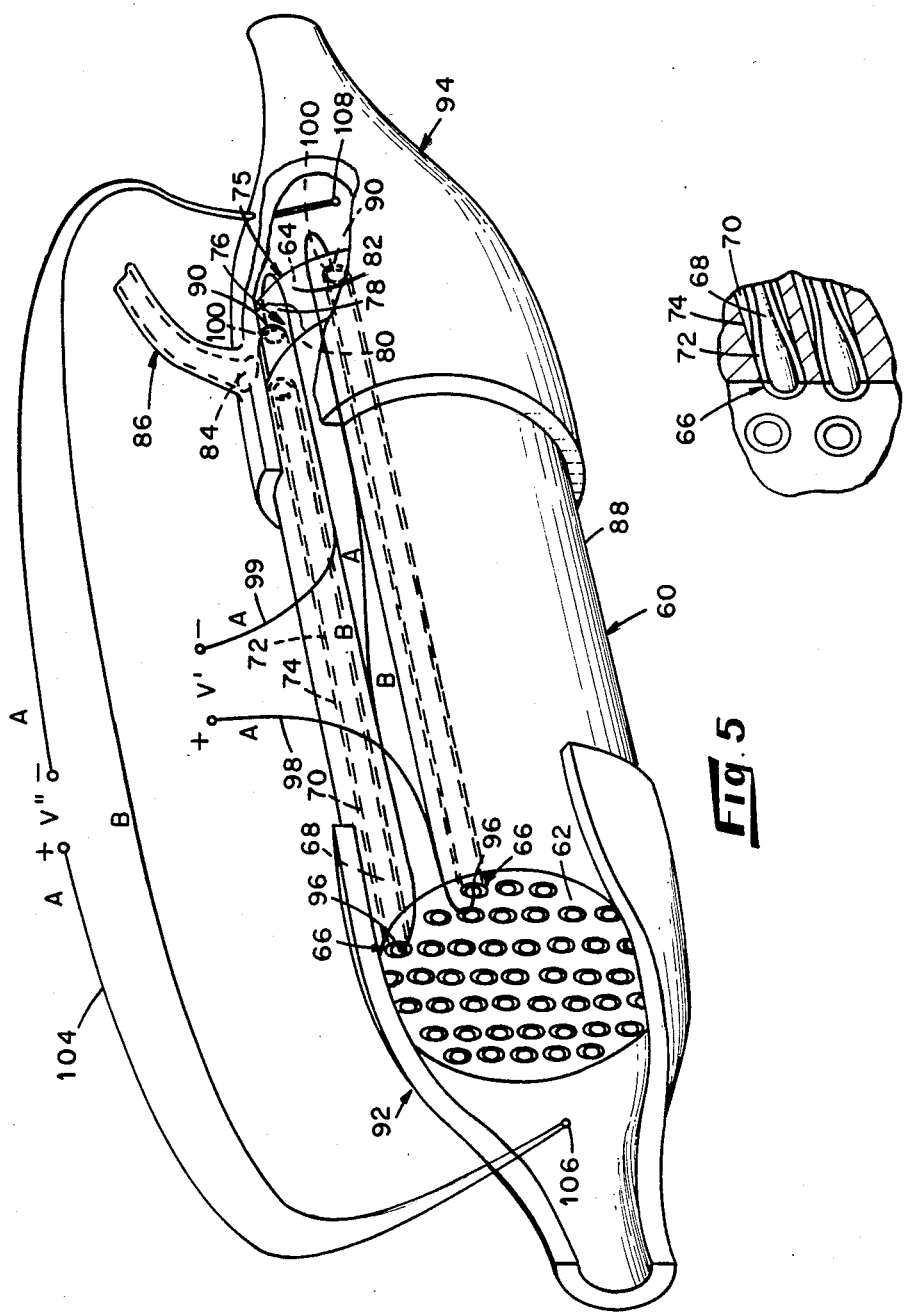

DEVICE FOR CONTINUOUS IN VIVO MEASUREMENT OF BLOOD GLUCOSE CONCENTRATIONS

DESCRIPTION

This invention relates to glucose measuring devices, and more specifically relates to a device for continuous in vivo measurement of blood glucose concentrations.

Background of the Invention

Measurement of blood glucose concentration is an important tool for diagnosing, treating or controlling a variety of disorders in which the glucose concentration is known to be an indicator of the existence or severity the condition. In the diabetic state, elevated levels of glucose in the blood are known to be indicative of diabetes mellitus characterized by hyperglycemia and glycosuria, and resulting from inadequate production or utilization of insulin. At the other extreme, abnormally low glucose concentrations are an indication of hypoglycemia or a deficiency of sugar in the blood which can be caused by over production of insulin. Substantial research efforts have been directed to the cause or causes of the diabetic condition, as well as methods and devices for treating and controlling the disease. Of the latter efforts, particular attention has been directed to methods and devices for measuring the levels of glucose present in the blood for use in controlling dietary intake; or where insulin is required, for controlling the frequency and amount of insulin which may be required to maintain the blood glucose concentration within an acceptable range. Adequate control of blood glucose is known to permit those afflicted with diabetes to lead a substantially normal life, delaying or eliminating the onset and reducing the severity of its devastating complications.

Known methods for measuring blood glucose have generally been directed to the use of electrodes for measuring oxygen depletion or hydrogen peroxide production, which is known to represent some function of the glucose concentration according to the well known glucose oxidation reaction as follows:

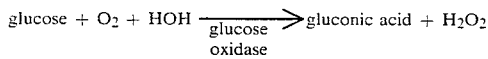

$$\text{glucose} + O_2 + HOH \xrightarrow[\text{oxidase}]{\text{glucose}} \text{gluconic acid} + H_2O_2$$

Various methods and devices employing measurement of either oxygen depletion or hydrogen peroxide production according to the reaction above are disclosed in U.S. Pat. Nos. 4,240,438 to Updike et al, 4,431,004 to Bessman et al, and 4,458,686 to Clark. These patents generally employ some type of selectively permeable membrane to separate the blood or body fluid from the enzyme, permitting blood constituents such as glucose to pass into the area of the enzyme where the oxidation reaction occurs. However, measurement of oxidation depletion is an indirect measurement of glucose concentration, and it is known that substantial problems exist with measurement of oxygen concentrations in the presence of other interfering biological substances, such as urea and amino acids which may also diffuse through the membrane.

Of the patents listed above, only Bessman suggests that the sensor is implantable. But the disclosure therein points out no means by which the sensor could be implanted to produce in vivo continuous measurement of blood glucose concentration.

In U.S. Pat. No. 4,436,094 to Cerami an in vivo glucose monitor is disclosed employing a charge transfer medium comprising a reversible complex of a binding macromolecular component, and an electrical charge bearing carbohydrate component. Increases in glucose level are reflected in the release of the charge-bearing carbohydrate to the electrical field of the monitor. Again, Cerami involves the use of an electrode in a complicated chemical environment and the attendant problems that exist with electrodes, such as discussed above. Further variations in the use of electrodes have been proposed by Richter et al in U.S. Pat. Nos. 4,366,033 and 4,477,314.

A membrane electrode for direct potentiometric or polarographic measurement of glucose is disclosed in U.S. Pat. No. 4,440,175 to Wilkins which is said to offer advantages over indirect measurement of glucose such as those which employ oxygen sensitive electrodes. However, Wilkins is still another application of species-sensitive electrodes with their known problems.

Of the above patents, only Bessman et al, Cerami, and Wilkens speak of application of the sensor in vivo. But none of the disclosures say how their technique would be performed in vivo.

Another potentially useful measurement for glucose involves measurement of the heat generated by the glucose oxidase reaction. See, Danielsson, B., Mattieson, B., Karlsson, R., and Winquist, F. "Bio-technology and Bio-engineering" Vol. XXI, page 1749–1766 (1979) John Wiley and Sons, Inc. The above reference was incorporated into the disclosure of Bessman et al. However, the Danielsson et al reference discloses only an enzyme thermiston for a continuous measurement of glucose with no mention therein of in vivo measurements. Also, the thermiston requires an independent current source making it ill-suited for in vivo applications.

The above shortcomings present in methods and devices for measuring glucose have tended to limit the usefulness of such devices for in vivo continuous measurement of glucose concentrations. The devices are relatively complex, and are subject to a number of inaccuracies due to their sensitivities and the complicated bio-chemical environment in which in vivo measurements must be made.

Thus, a need exists for a device for continuous, in vivo measurement of blood glucose concentrations which is not subject to the inherent inaccuracies and instabilities which have heretofore been attendant glucose measuring devices and methods. The present invention meets these needs, among others, through provision of a device for continuous in vivo measurement of blood glucose concentration, the device being capable of independently producing a signal which is a function of the glucose concentration without the inherent inaccuracies and instabilities which have heretofore plagued glucose monitoring devices, especially those employing electrodes.

Summary of the Invention

In accordance with a preferred form of the invention, a device is disclosed for continuous in vivo measurement of blood glucose concentration. At least one elongate double passageway is preferably a double-lumened tube having a first lumen thereof in flow communication with one or more small arteries to receive and conduct a flow of blood through the tube, and to deliver the flow of blood out of the tube and back to one or more veins. A semi-permeable membrane wall is located within the double-lumened tube to separate the first limen from a second lumen, with the membrane wall being permeable to permit diffusion therethrough of glucose. A quantity of enzyme, preferably glucose oxidase, is located within the second lumen for catalyzing the oxidation of glucose diffusing into the second lumen to generate heat. The double-lumened tube is insulated to substantially eliminate radial heat transfer out of the tube. Means are provided for measuring the increase in temperature of blood passing through the first lumen, preferably entry and exit micro-thermocouple junctions or solid state temperature sensors with the entry micro-thermocouple junction being positioned in the vicinity of the entrance of blood into the first lumen and the exit micro-thermocouple junction being positioned in the vicinity of the exit of blood from the first lumen, the micro-thermocouple junctions being interconnected to produce a voltage signal. When the device is located in vivo with the first lumen configured as described, glucose within the blood flowing in the first lumen diffuses through the membrane wall into the second lumen and is oxidized, generating heat and causing an increase in the temperature of blood flowing in the first lumen. The magnitude of the temperature increase measured by the thermocouples is a function of the glucose concentration in the blood and can then be utilized to control an insulin reservoir pump to maintain a proper glucose concentration in the blood. Since the double-lumened tube is insulated, the heat generated by the oxidation reaction is transferred into the blood flowing in the first lumen so that substantially all of the heat generated is reflected in a temperature rise of the blood as it passes through the first lumen giving a reliable indicator of the glucose concentration. And, the signal produced by the thermocouples is a direct function of the glucose consumed and is not subject to the inaccuracies and sensitivities which plague specie-sensitive electrodes which have been used in the past.

In accordance with another aspect of the invention, the second lumen of the tube is an outer lumen having an elongate, annular configuration and the first lumen is an inner lumen having an elongate, cylindrical configuration with the outer lumen being generally concentrically located about the inner lumen. The semi-permeable membrane wall is configured as a tubule and is located between the inner and outer lumens. The diameter of the inner lumen is small compared to its length so that blood flowing through the inner lumen is exposed to a relatively large surface area of membrane and the glucose is permitted to diffuse symmetrically radially outwardly of the inner lumen through the membrane to enable more complete diffusion and oxidation of the glucose within the blood. Preferably the length to diameter ratio of the inner lumen is on the order of 25 to 1, or greater.

In accordance with a further aspect of the invention, a subcutaneous reservoir is provided for receiving and containing by injection through the skin a supply of replacement enzyme and an enzyme delivery tube interconnects the reservoir and the outer lumen. This permits periodic introduction of fresh enzyme into the outer lumen to insure that a relatively constant degree of glucose conversion is maintained.

In accordance with yet another aspect of the invention, a device is disclosed for continuous, in vivo measurement of glucose concentration and includes a module having a plurality of elongate, double-lumened tubes with the tubes extending through the module from an entry end thereof to an exit end thereof. The tubes have outer lumens generally concentrically disposed of inner lumens with the inner and outer lumens being separated by semi-permeable membrane tubules permeable to permit diffusion of glucose from the inner lumens to the outer lumens. The inner lumens are configured to be in flow communication with one or more small arteries to receive and conduct a flow of blood through the double-lumened tubes, and to deliver the flow of blood back to one or more veins. A quantity of enzyme, preferably glucose oxidase, is located in the outer lumens for catalyzing the oxidation of glucose diffusing into the outer lumens to generate heat and means are provided for substantially eliminating heat transfer out of each of the tubes, preferably by selection of a material for the module which is substantially non-heat conducting. Further means are provided for producing a signal having a magnitude proportionate to the magnitude of the temperature increase of blood flowing through the inner lumens, preferably a series connection of thermocouple junctions. When the device is located in vivo with the inner lumens configured as described, glucose within the blood flowing in the inner lumens diffuses through the membrane tubules into the outer lumens and is oxidized, generating heat and causing an increase in the temperature of blood flowing in the inner lumens. The magnitude of the signal produced by the series connection of thermocouple junctions or solid state temperature sensors is a function of the glucose concentration in the blood. Among the advantages offered by this aspect of the invention is the capability of obtaining a signal proportionate to the glucose concentration which is approximately equal to the combined magnitudes of the signals produced by the individual thermocouple junctions so that even small temperature increases within the individual double-lumened tubes can be utilized collectively to produce a signal that is a reliable indicator of the blood glucose concentration. Further, the collective surface area of membrane exposed to the blood flow as provided by the individual membrane tubules results in substantially complete diffusion of glucose within the blood into the outer lumens whereupon oxidation of the glucose that has diffused into the outer lumens and the consequent temperature increase of the blood in the inner lumens produces a signal which is an reliable indicator of the absolute blood glucose concentration.

These and other advantages and aspects of the present invention will be readily appreciated by those of ordinary skill in the art as the same becomes better understood by reference to the following detailed description when considered in conjunction with the accompanied drawings in which:

BRIEF DESCRIPTION OF THE DRAWINGS

FIG. 5 is a perspective view of another form of the glucose measuring device illustrating a module containing a plurality of double lumened tubes with an inner lumen of each tube being separated from an outer lumen thereof by a membrane tubule permeable to glucose, and showing a portion of a series combination of several identical micro-thermocouple junctions to provide a larger temperature measurement signal; and FIG. 6 is a fragmentary cross sectional view of the module of FIG. 5 illustrating a preferred form of attaching the membrane tubules to cylindrical walls defining the double-lumened tubes.

DESCRIPTION OF PREFERRED EMBODIMENTS

Figure 1:
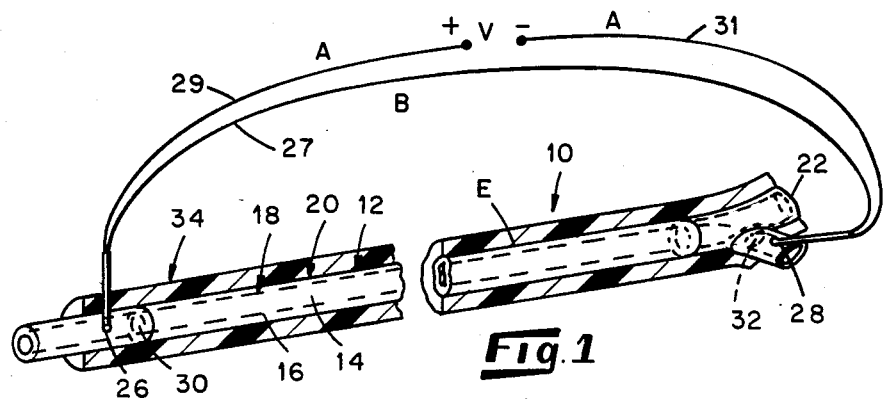
FIG. 1 is a somewhat diagrammatic perspective view, partially in cross section, of one form of a glucose measuring device according to the present invention illustrating an insulated double-lumened tube containing a quantity of glucose oxidase enzyme in an outer lumen which is separated from an inner lumen by a glucose permeable membrane tubule, the inner lumen being configured to conduct a flow of blood through the device and micro-thermocouples being located adjacent the entrance and exit of blood into and from the inner lumen.
Figure 2:
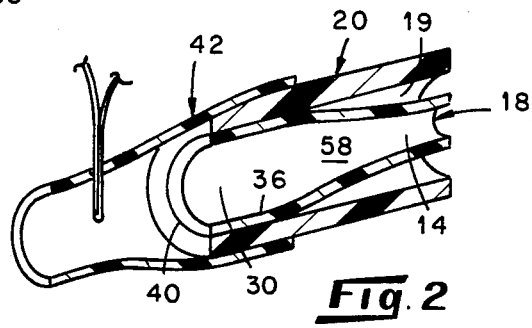
FIG. 2 is a fragmentary perspective view in cross section of the area of the glucose measuring device of FIG. 1 adjacent the entrance of blood into the inner lumen.
Figure 3:
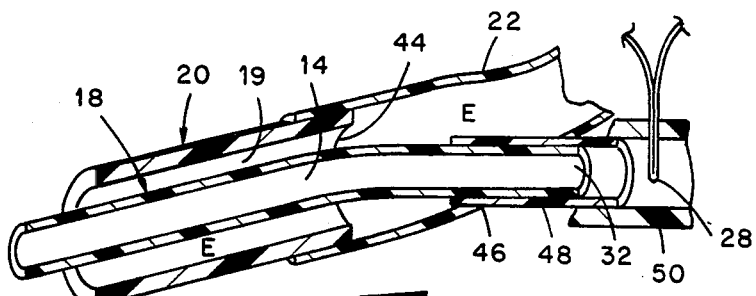
FIG. 3 is a fragmentary perspective view in cross section of the area of the glucose measuring device of FIG. 1 adjacent the exit of blood from the inner lumen.

Referring now to the drawings in which like reference characters refer to like or similar parts throughout the several views, there are shown in FIGS. 1 through 3 various views of a glucose measuring device 10 according to a preferred form of the present invention. A double-lumened tube 12 includes an inner lumen 14 and an outer lumen 16 with a membrane tubule 18 separating the outer lumen 16 from the inner lumen 14. A flow of arterial blood is conducted to the inner lumen 14 from an anastomosis with a small artery (not shown) and is conducted therefrom to an anastomosis with a small vein (not shown). The membrane tubule 18 is selectively permeable to blood constituents of lower molecular weight, including glucose. Suitable membranes for use in the device 10 are prefabricated tubules formed from materials such as cellulose, cellulose acetate, cuprammonium rayon, or similar synthetic material having a preferred thickness of about 10 to $20 \times 10^{-6}$ m with a diffusion rate of glucose in the range of 100 to 120 ml/min/m$^2$.

A quantity of enzyme E, preferably glucose oxidase stabilized in a suitable buffer solution, is confined between the membrane tubule 18 and an inner wall 19 of an outer cylindrical, non-porous tube 20 defining the overall diameter of the double-lumen tube 12. Enzyme E is delivered to the device 10 by means of a non-porous delivery tube 22 connected to a subcutaneous reservoir 24 (see FIG. 4) to which is delivered a supply of enzyme E for replenishing spent enzyme E contained within the device 10. A pair of micro-thermocouple junctions 26 and 28 are located adjacent an entrance opening 30 of the inner lumen 14 and an exit opening 32 of the inner lumen 14, respectively. Glucose within the blood passing from the entrance opening 30 of the inner lumen 14 to the exit opening 32 thereof diffuses through the membrane 18 into the outer lumen 16 where the enzyme E catalyzes the oxidation of the glucose into gluconic acid and hydrogen peroxide with a attendant release of energy in the form of heat. The gluconic acid and hydrogen peroxide diffuse away from the outer lumen 16 through the membrane tubule tube 18 and back into the blood flow. If desired, a quantity of catalase can be added to the enzyme E for decomposing the hydrogen peroxide. An insulation wrap 34 surrounds the device 10 at least from a point ahead of the micro-thermocouple junction 26 to a point downstream of the micro-thermocouple junction 28 so that the heat liberated by the oxidation of glucose cannot pass outwardly of the device 10, but instead is transferred to the blood flowing in the inner lumen 14. The resulting heat transfer causes a rise in temperature of the blood which is detected by the arrangement of the micro-thermocouples 26 and 28. This increase in temperature is a function of the glucose concentration in the blood.

Referring now to FIG. 2, the area of the device 10 adjacent the entry opening 30 of the inner lumen 14 is illustrated. The insulation 34 is removed for clarity. As is shown, the membrane tubule 18 is expanded somewhat at its forward end 36 and bonded by application of heat or a suitable adhesive around its periphery at its forward end 36 to the inner wall 19 of the outer tube 20. This bonding location of the membrane tubule 18 to the outer tube 20 constitutes a preferred form of confining the enzyme E within the outer lumen 16. To enable bonding, the membrane tubule 18 may be stretched radially outwardly adjacent a forward opening 40 of the tube 20 against the inner surface 19 of the tube 20 subsequent to application of adhesive along the inner surface 19 into the tube 20 a sufficient distance to insure an adequate bond. Then, any remaining portion of the membrane tubule 18 extending out of the open end 40 of the tube 20 can be trimmed so that the membrane tubule 18 is flush with the outer tube 20. An arterial adapting tube 42 has one of its ends stretched over the open end 40 of the outer tube 20 and is sealably connected thereto such as by use of a suitable adhesive to bond the arterial adapter 42 to the outer tube 20. The other end of the arterial adapter 42 is connected to a small artery by anastomosis according to well known surgical procedures. It is seen that with the membrane tubule 18 attached to the outer tube 20 in this manner, the blood entering the inner lumen 14 is prevented from contacting the enzyme E contained within the outer lumen 16. This substantially eliminates any possibility of the enzyme E contaminating the blood, providing one means by which the device 10 is biologically compatible for in vivo glucose measurements. The micro-thermocouple junction 26 adjacent the entrance opening 30 is positioned a sufficient distance upstream of the area of enzymatic activity so that any heat generated by the glucose oxidation cannot migrate into the area of the micro-thermocouple junction 26 and thereby affect its reading.

Reference is now had to FIG. 3 where the configuration of the device 10 in the area of the exit opening 32 of the inner lumen 14 is shown in detail. The membrane tubule 18 is seen extending out of an open end 44 of the outer tube 20 through an opening 46 in the wall of the enzyme delivery tube 22. A non-porous sleeve 48 may be employed to connect the membrane tubule 18 to a venous delivery tube 50 which is connected to a small vein by anastomosis according to well known surgical procedures. Alternately, the venous delivery tube 50 may extend through the wall of the enzyme delivery tube 22 to receive within the venous delivery tube 50 the exit end of the membrane tubule 18. In any case, provision is made to insure that the membrane tubule 18 is not exposed to the biological tissue in which the device 10 is embedded to prevent undesired diffusion of blood constituents through the membrane tubule 18.

The membrane tubule 18, sleeve 48, and venous deliver tube 50 are preferably connected by forming a bond between the surfaces in contact using a suitable adhesive. The exit of the sleeve 48 or the venous delivery tube 50 from the enzyme delivery tube 22, as the case may be, through the opening 46 is sealed such as by application of adhesive thereat or by applying heat to the area of the opening 46 to partially melt the material so that a bond is formed therebetween. The enzyme delivery tube 22 is positioned over the open end 44 of the outer tube 20 in substantially the same manner as described above in FIG. 2 with reference to the arterial tube 42. The micro-thermocouple junction 28 is positioned just downstream of the exit opening 32 of the membrane tubule 18. And, as was described above with reference to FIG. 1, the device 10 is insulated at least to a point downstream of the micro-thermocouple junction 28. Thus, substantially all of the heat generated by the oxidation of glucose in the outer lumen 16 will be reflected in a rise of the temperature of of blood flowing in the inner lumen 14.

Figure 4:
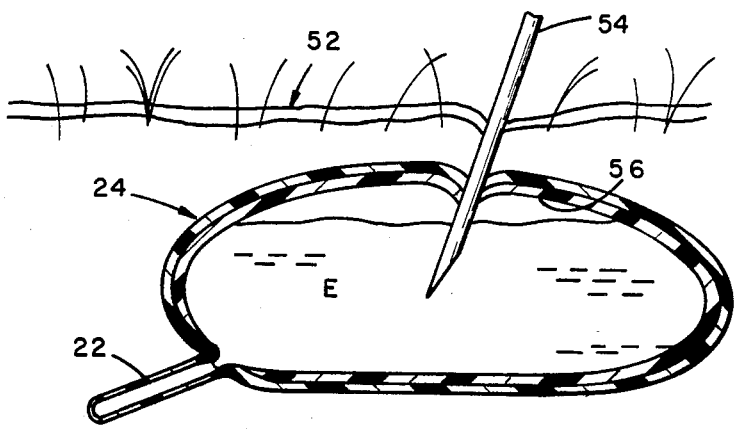
FIG. 4 is a cross sectional view of a subcutaneous reservoir for receiving and containing a supply of enzyme and for delivering the enzyme to the outer lumen.

Referring now to FIG. 4, the subcutaneous reservoir 24 is illustrated surgically embedded beneath a skin surface 52 for storing a supply of enzyme E to replenish spent enzyme within the outer lumen 16. In a known manner, enzyme E is injected into the reservoir 24 by use of a needle 54, the reservoir 24 having self-sealing walls 56 to prevent escape of enzyme after withdrawal of the needle 54 from the reservoir 24.

Referring now generally to FIGS. 1 through 4 where various aspects of one form of the glucose monitoring device 10 have been described, it is to be appreciated that the double-lumened tube 12 and its insulation covering 34 combine to form an overall diameter of the device 10, excluding the insulation 34, that is preferably in the neighborhood of 0.5 to 2.0 mm. The overall length of the device 10 is preferably 50 to 100 mm, wherein it is seen that the double-lumened tube 12 is sized so that when surgically embedded, it is practically unnoticed.

The length of the inner lumen 14 is approximately equal to the length of the device 10 and its diameter is selected to provide sufficient surface area along an inner wall 58 of the membrane tubule 18 to insure diffusion of a substantial portion of the glucose within the blood into the outer lumen 16. To this end, the membrane tubule 18 preferably has an inner diameter of about 0.3 to 1. mm and thus a surface area of about 50 to 500 mm$^2$ along its inner surface 58.

An artery of suitable size and flow is selected to obtain a preferred blood flow through the inner lumen of about 20 ml/min, the pressure loss between the entrance and exit locations of the inner lumen 14 being advantageously maintained at about 60 to 80 mm Hg. Through the use of a suitable membrane material for the tubule 18, examples of which were given above, this should provide a glucose clearance value in the order of 5 to 10 ml/min; that is, 50 to 10 ml of blood in the total blood flow through the device 10 will be cleared of glucose. Thus, with a blood glucose concentration of about 1 mg/ml and a clearance value of about 5 ml/min, approximately 5 mg of glucose per minute should diffuse through the tubule 18 into the outer lumen 16, and when the clearance value is about 10 ml/min, approximately 10 mg of glucose per minute will diffuse.

Whatever clearance value is obtained through the arrangement as described, it is substantially constant, so that increases in blood glucose concentration produce a corresponding proportional increase in the amount of glucose diffusing into the outer lumen 16. Further, a substantially constant rate of oxidation of glucose in the outer lumen 16 is insured by maintaining a relatively large excess of enzyme E within the outer lumen 16 over that which would be expected to produce complete oxidation under these conditions. This excess of enzyme E, in combination with the length of the tubule 18, aids in maintaining a continual gradient of glucose concentration across the wall of the tubule 18 to induce a mass transfer of glucose into the outer lumen 16 generally along the entire length of inner lumen 14.

The micro-thermocouple junctions 26 and 28 are arranged in a conventional manner in that the junctions 26 and 28 are interconnected by a wire 27 constructed of a B type metal and lead wires 27 and 29 are constructed of an A type metal. The A and B metal types are chosen to produce the thermocouple junctions that produce an EMF proportional to the temperature difference between the junction. For example the A and B type metals may be alumel and chromel. In the circuit shown in FIG. 1, the EMF produced by the junctions 26 and 28 are of opposite polarity so that the voltage V between lead wires 29 and 31 is a differential voltage whose magnitude is proportional to the difference in temperature between junctions 26 and 28. Thus, the voltage V between lead wires 29 and 31 is proportional to the amount of glucose in the blood. This voltage V may be monitored by appropriate instruments, such as an appropriately calibrated volt meter, to provide a continuous indication of the glucose levels in the blood. Alternately, the voltage V can be applied directly to an insulin reservoir/pump circuit with the latter having incorporated therein appropriate logic to cause the insulin pump to supply an amount of insulin to the blood as needed.

An alternate embodiment of the glucose measuring device 10' will now be described with reference to FIGS. 5 and 6. The device 10' includes an elongate cylindrical module 60 having a forward end 62, preferably defined by a planar surface, and a rearward end 64, also a planar surface. Incorporated within the module 60 and extending longitudinally therethrough are a plurality of double-lumened tubes 66, only two of which are indicated by the number 66 for the purposes of clarity. Each of the double-lumened tubes 66 comprises an inner lumen 68 and an outer lumen 70 with an elongate membrane tubule 72 being located within the double-lumened tube 66 concentric with a cylindrical wall 74 defining the outer diameter of the double-lumened tube 66 to separate the inner lumen 68 from the outer lumen 70 to contain a quantity of enzyme E within the outer lumens 70. As shown in FIG. 6, the membrane tubule 72 is attached to the inner wall 74 in much the same manner as is the membrane tubule 18 described with reference to FIG. 2.

A cavity 76 of the module 60 communicates with the outer lumens 70 and contains a supply of replacement enzyme E. The cavity 76 is formed inside of the rearward end 64 and extends axially from an inside wall 78 of the end 64 to a front wall 80, spaced forwardly of and oriented generally co-planar with the inside wall 78. A cylindrical band 82 circumferentially encloses the cavity 76 with an opening 84 being formed in the band 82 to permit communication between the cavity 76 and an enzyme delivery tube 86. The band 82 and rearward end 64 are preferably constructed separately of a body portion 88 of the module 60 to form a cap portion 75 thereof. A plurality of circular openings 90 are formed in the rearward end 64 and are spaced and arranged across the surface of the end 64 complementary of the open ends of the double-lumened tubes 66 at the front wall 80 of the cavity 76. The cap 75 is attached to the body 88 with the openings 90 aligned with the open ends of the double-lumened tubes 66. In manufacturing the module 60, the membrane tubules 72 may first be bonded to the walls 74 as shown in FIG. 6 with the initial length of the membrane tubules 72 being somewhat longer than that of the module 60. Prior to attachment of the cap 75 to the body 88, each individual membrane tubule 72 is positioned within one of the openings 90 in the cap 75. Then, the cap 75 is attached to the body 88 and the membrane tubules 72 are pulled rearwardly of the openings 90 so that they are relatively taut and generally concentrically located of the walls 74. Then, the membrane tubules 72 are bonded to the openings 90, thereby preventing escape of the enzyme from the cavity 76 into the blood exiting the inner lumens 68 at the rearward end 64 of the module 60.

A non-porous arterial delivery tube 92 is stretched over the front end 62 of the module 60 and is connected to a small artery by anastomosis as described above with reference to FIG. 1. Likewise, a non-porous venous delivery tube 94 delivers blood exiting the inner lumens 68 of the module 60 to a small vein and is connected thereto by an anastomosis.

The enzyme delivery tube 86 delivers the supply of enzyme E, preferably glucose oxidase and catalase, from a subcutaneous reservoir such as the reservoir 24 illustrated in FIG. 4 into the cavity 76. The outer lumens 70 are open to the cavity 76 at the front wall 80 of the cavity 76 to permit movement of enzyme E from the cavity 76 into the annular areas of the outer lumens 70. Preferably, the enzyme delivery tube 86 is formed as part of the venous delivery tube 94 and opens into the inner cylindrical wall of the venous delivery tube 94 for being positioned in communication with the opening 84 of the cylindrical band as shown. The cavity 76 is maintained substantially full of replacement enzyme E at all times to create an excess of enzyme E within the outer lumens 70 which helps to insure substantially complete oxidation of glucose.

In a preferred form of the module 60, 50 to 100 double-lumened tubes 66 are formed within the body 88. Preferably, the material forming the body 88 is a non-porous material which is substantially non-heat conducting, such as the synthetic material sold under the trdemark Dacron, to substantially eliminate the existence of a heat sink for absorbing heat produced during the oxidation of glucose within the outer lumens 70. In this regard, an insulating layer (not shown) should also be employed surrounding the glucose measuring device 10' to substantially eliminate heat transfer radially outwardly from the module 60.

The module 60 has a preferred diameter of about 2 cm with the outer diameter of each individual outer lumen 70 as defined by the diameters of the cylindrical walls 74 of the double-lumened tubes 66 being in the neighborhood of 0.5 to 2.0 mm. The membrane tubules 77 are preferably constructed and proportioned generally the same as the tubule 18 described above so that each tubule 77 has an inside surface area of approximately 50 to 500 $mm^2$ for a total available surface area of membrane within the module 60 for diffusion of glucose into an area of enzymatic activity of about 25 to 500 $cm^2$.

Thus, there exists in the preferred form of the device 10' a relatively large surface area of membrane in contact with the blood in proportion to the overall length of the device 10', which offers a much greater glucose clearance value than a single tube having the same or similar length. This offers an advantage over the use of a single tube where it is desired to measure the glucose concentration at a higher clearance value than can be achieved with a single tube arrangement.

A preferred means for producing a signal which is a function of the blood glucose concentration is provided by a series of micro-thermocouple junctions connected between lead wires 98 and 99, only two locations of which are illustrated in FIG. 5 for the purpose of clarity. Forward junctions 96 are located adjacent the entrance of blood into each of the inner lumens 68 and rearward junctions 100 are located adjacent the exit of blood from the inner lumens 68. The junctions 96 and 100 are formed by connections between A and B type material as previously described with regard to FIG. 1. The junctions 96 and 100 for each lumen 68 is a junction pair, and each junction pair are connected by a wire of B type material. The junction pairs are connected in series so that the differential voltages produced by each junction pair are added providing for a voltage V' between lead wires 98 and 99 which is the sum of the voltages produced by the junction pairs. To create the series connection, each rearward junction 100 is connected by an A type wire to a forward junction 96 of a different lumen 68, except that the first forward junction 96 in the series is connected to lead wire 98 and the last rearward junction 100 in the series is connected to lead wire 99. This arrangement makes it possible to obtain a signal from the device 10' even when the temperature increase of the blood flowing through the inner lumens 68 is very small. Also, the series connection of numerous thermocouple junction pairs has an averaging effect. If one pair produced an erroneous signal, that one erroneous signal would be only a part of the total voltage V' between lead wires 98 and 99.

Alternately, a single pair of micro-thermocouple junctions 104 are employed having an entrance junction 106 and an exit junction 108 which function generally in the same manner as the junctions 26 and 28 shown in FIG. 1 to produce a single voltage V' representative of the blood glucose concentration.

All of the materials employed in constructing the device 10 are selected to be biologically compatible for in vivo residence, and many such materials are known to be suitable and commonly available. Also, the wires forming the micro-thermocouple arrangements are insulated so that thermocouple junctions are electrically isolated from blood and other body fluids, and other necessary provisions are made, where necessary, to eliminate biological interferences with the operation of the device 10.

Although particular embodiments of the glucose measuring device have been described in the foregoing detailed description, it will be understood that the device is capable of numerous rearrangements, modifications and substitutions of parts without departing form the scope of the invention according to what is claimed below.

What is claimed:

1. A device for continuous in vivo measurement of blood glucose concentration, comprising:
   at least one elongate, double passageway having a first passageway adapted to be in flow communication with one or more small arteries to receive and conduct a flow of blood and to deliver the flow of blood back to one or more veins, and having a second passageway adjacent said first passageway;

a semi-permeable membrane wall located within said double passageway to separate said first passageway from said second passageway, said membrane wall being permeable to permit diffusion therethrough of glucose;

a quantity of enzyme located within said second passageway for catalyzing the oxidation of glucose diffusing into said second passageway to generate heat;

means for insulating said double passageway to substantially eliminate radial heat transfer out of said double passageway; and means for measuring the increase in temperature of blood passing through said first passageway, whereby glucose within the blood flowing in said first passageway diffuses through said membrane wall into said second passageway and is oxidized, generating heat and causing an increase in the temperature of blood flowing in said first passageway, with the magnitude of the increase measured by said means for measuring being a function of the glucose concentration in the blood.

2. The device of claim 1, wherein said means for measuring comprises entry and exit micro-thermocouple junctions, said entry micro-thermocouple junction being positioned in the vicinity of the entrance of blood into said first passageway and said exit micro-thermocouple junction being positioned in the vicinity of the exit of blood from said first passageway, said micro-thermocouple junctions being interconnected to produce a voltage signal corresponding to the increase in temperature of blood flowing through said first passageway.

3. The device of claim 1, further comprising:

said second passageway being an outer lumen having an elongate, annular configuration, and said first passageway being an inner lumen having an elongate, cylindrical configuration with said outer lumen being generally concentrically located about said inner lumen; and said semi-permeable membrane wall being configured as a tubule and located between said inner and outer lumens.

4. The device of claim 3, wherein said means for measuring comprises entry and exit micro-thermocouple junctions, said entry micro-thermocouple junction being positioned in the vicinity of the entrance of blood into said first lumen and said exit micro-themocouple junction being positioned in the vicinity of the exit of blood from said first lumen, said micro-thermocouple junctions being interconnected to produce a voltage signal corresponding to the increase in temperature of blood flowing through said first lumen.

5. The device of claim 1, further comprising means for delivering replacement enzyme to said second passageway.

6. The device of claim 5, wherein said means for delivering comprises:

a subcutaneous reservoir for receiving and containing by injection through the skin a supply of replacement enzyme; and an enzyme delivery tube interconnecting said reservoir and said second passageway.

7. The device of claim 1, wherein said enzyme comprises glucose oxidase.

8. The device of claim 1, wherein said enzyme comprises glucose oxidase with catalase being added to decompose hydrogen peroxide produced when the glucose is oxidized.

9. A device for continuous, in vivo measurement of glucose concentration, comprising:

a module having a plurality of elongate, double-lumened tubes with said tubes extending through said module from an entry end thereof to an exit end thereof, said tubes having outer lumens generally concentrically disposed of inner lumens that are defined by semi-permeable membrane tubules permeable to permit diffusion of glucose from said inner lumens to said outer lumens;

said inner lumens adapted to be in flow communication with one or more small arteries to receive and conduct a flow of blood through said double-lumened tubes, and to deliver the flow of blood back to one or more veins;

a quantity of enzyme located in said outer lumens for catalyzing the oxidation of glucose diffusing into said outer lumens to generate heat;

means for substantially eliminating radial heat transfer out of each of said tubes; and means for producing a signal having a magnitude proportionate to the magnitude of the temperature increase of blood flowing through said inner lumens, whereby glucose within the blood flowing in said inner lumens diffuses through said membrane tubules into said outer lumens and is oxidized, generating heat and causing an increase in the temperatue of blood flowing in said inner lumens, with the magnitude of said signal being a function of the glucose concentration in the blood.

10. The device of claim 9, wherein said means for producing a signal comprises a plurality of micro-thermocouple junctions with one entry junction being located in the vicinity of the entrance of blood into each one of said inner lumens and one exit junction being located in the vicinity of the exit of blood out of each of said inner lumens, said plurality of micro-thermocouple junctions being interconnected in series with each entry junction being individually connected to the corresponding exit junction of the same inner lumen at which the junctions are positioned to form a junction pair, said junction pairs being connected in series, whereby the magnitude of the voltage signal produced by said plurality of micro-thermocouple junctions is equal to the combined magnitudes of the voltage signals produced by the junction pairs.

11. The device of claim 9, further comprising a cavity formed in said module for receiving and containing a supply of enzyme, said outer lumens being in communication with said cavity so that enzyme within said cavity enters and fills said outer lumens to maintain an excess of enzyme in said outer lumens.

12. The device of claim 11, further comprising:

a subcutaneous resrvoir for being filled with enzyme by injection of enzyme from a needle made to enter said reservoir; and an enzyme delivery tube inteconnecting said reservoir and said cavity of said module for delivering enzyme to said cavity from said reservoir.

* * * * *

UNITED STATES PATENT AND TRADEMARK OFFICE
CERTIFICATE OF CORRECTION

PATENT NO. : 4,685,463
DATED : August 11, 1987
INVENTOR(S) : R. Bruce Williams

It is certified that error appears in the above-identified patent and that said Letters Patent is hereby corrected as shown below:

Column 2, line 35, "thermiston" should be --thermistor--.

Column 2, line 37, "thermiston" should be --thermistor--.

Column 3, line 5, "limen" should be --lumen--.

Column 7, line 48, "1." should be --1.5--.

Column 7, line 58, "50" should be --5--.

Signed and Sealed this

Eighth Day of December, 1987

Attest:

DONALD J. QUIGG

Attesting Officer

Commissioner of Patents and Trademarks